United States Patent [19]

Sogawa et al.

[11] Patent Number: 5,168,880
[45] Date of Patent: Dec. 8, 1992

[54] APPARATUS FOR DIELECTRIC-HEATING LIVING BODY BY HIGH-FREQUENCY CURRENT AND APPARATUS THEREFOR

[75] Inventors: Akira Sogawa, Tokyo; Tadashi Onuma, Inashiki; Atsushi Yoshihara, Hino; Kiyoshi Kitagawa, Chiba; Chikau Onodera, Nerima, all of Japan

[73] Assignee: Olympus Optical Co., Ltd., Tokyo, Japan

[21] Appl. No.: 584,648

[22] Filed: Sep. 19, 1990

Related U.S. Application Data

[63] Continuation-in-part of Ser. No. 282,857, Dec. 9, 1988, abandoned, which is a continuation of Ser. No. 74,544, Jul. 17, 1987, abandoned.

[30] Foreign Application Priority Data

Jul. 17, 1986 [JP] Japan .................................. 61-168466

[51] Int. Cl.$^5$ ............................................. A61N 5/00
[52] U.S. Cl. .................................. 128/784; 128/401; 128/804
[58] Field of Search ............................ 128/784–786, 128/804, 401

[56] References Cited

U.S. PATENT DOCUMENTS

| | | | |
|---|---|---|---|
| 4,528,991 | 7/1985 | Dittmar et al. | 128/804 |
| 4,662,383 | 5/1987 | Sogawa et al. | 128/784 |
| 4,676,258 | 6/1987 | Inokuchi et al. | 128/804 |

OTHER PUBLICATIONS

Brezovich et al, "A Practical System . . . Hyperthermia", Int. J. Rad. Onc. Biol. Phys., vol. 7, No. 3, pp. 423–430, Mar. 1981.

Primary Examiner—Lee S. Cohen
Attorney, Agent, or Firm—Oblon, Spivak, McClelland, Maier & Neustadt

[57] ABSTRACT

A method of heating a tract organ of the living body with high-frequency electric current, includes the step of controlling a flow volume of a coolant supplied into a first electrode so as to be substantially equal to that of a blood which flows in a living body tissue at a portion where the first electrode is disposed while controlling a temperature of the coolant to a temperature range of the living body tissue at the portion, the coolant being an aqueous solution of salts at a predetermined concentration.

The method makes it possible to effect safely a hyperthermic treatment.

An apparatus for carrying out the method is also disclosed.

2 Claims, 9 Drawing Sheets

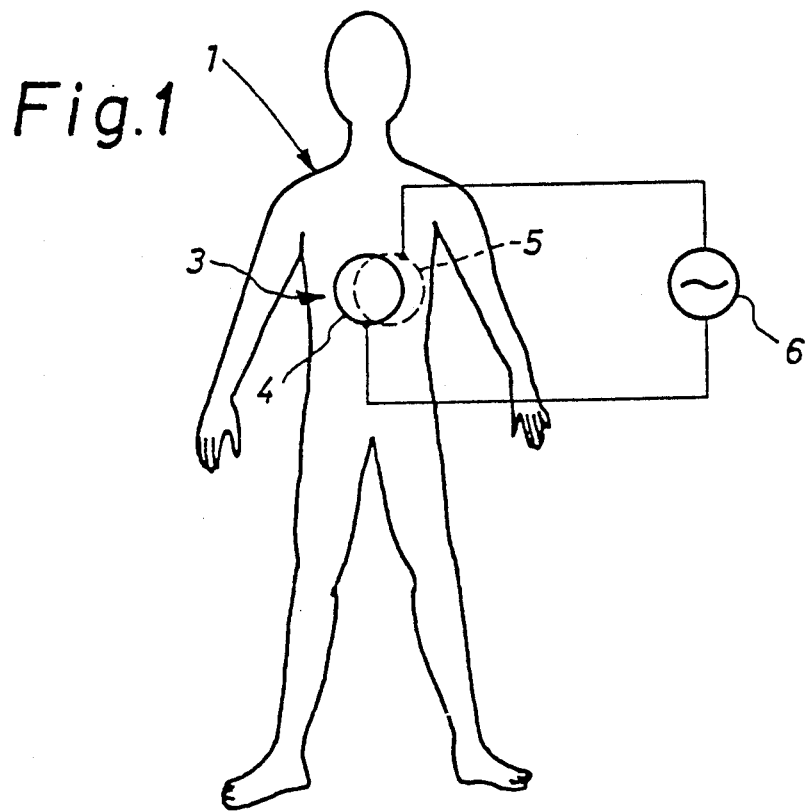
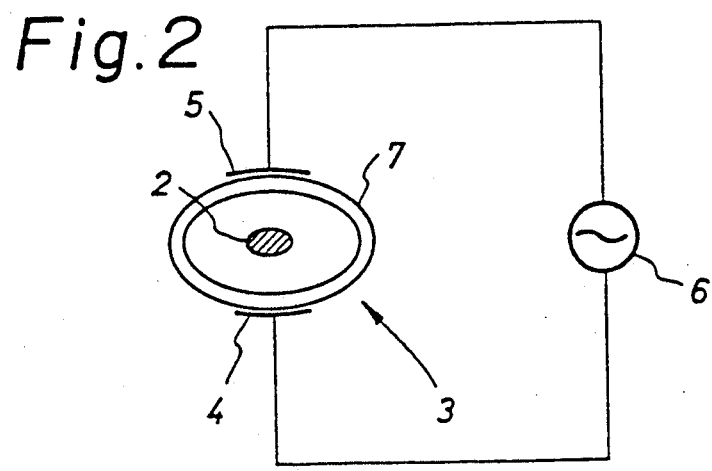

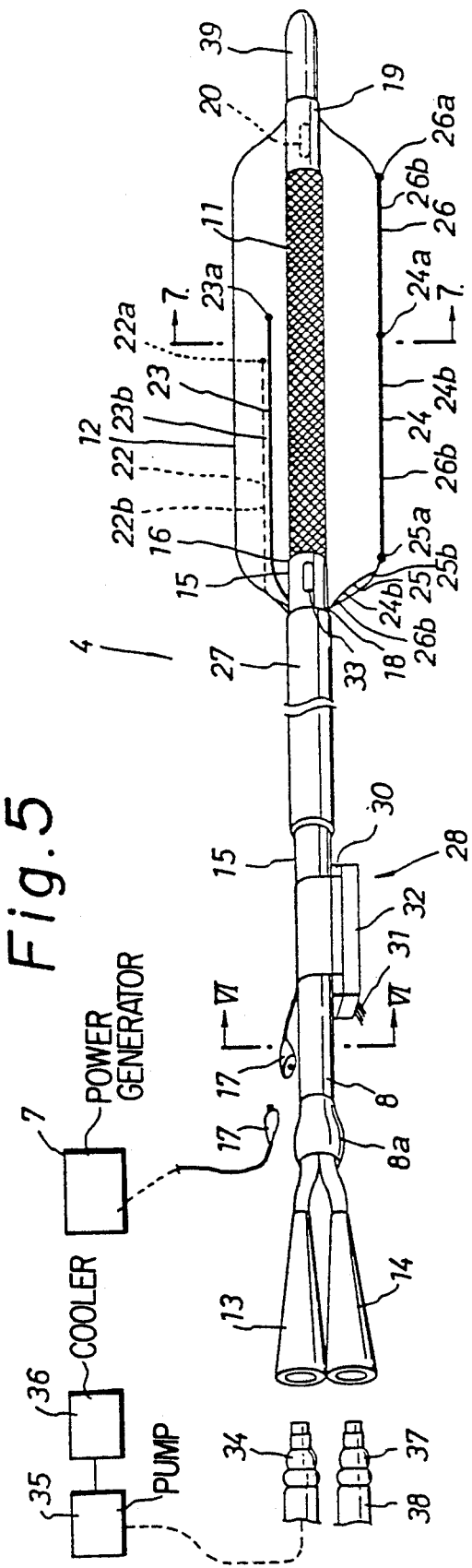
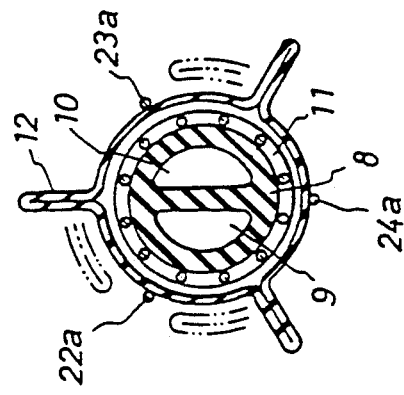
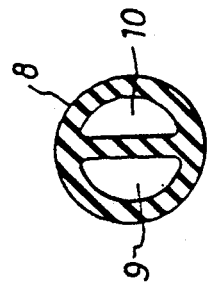

APPARATUS FOR DIELECTRIC-HEATING LIVING BODY BY HIGH-FREQUENCY CURRENT AND APPARATUS THEREFOR

CROSS-REFERENCE TO RELATED APPLICATION

The present application is a continuation-in-part of application Ser. No. 07/282,857 filed on Dec. 9, 1988, now abandoned, which is a file-wrapper continuation of application Ser. No. 07/074,544 filed on Jul. 17, 1987, now abandoned.

BACKGROUND OF THE INVENTION

The present invention concerns a method for heating a living body by high frequency current and an apparatus therefor.

The method of heating a living body by using high frequency current utilizes a phenomenon that high frequency current changes to heat when applied to a dielectric substance such as the living body and many reports have been presented in recent years for the therapeutical effect of the method on malignant tumors.

In the conventional high frequency heating method, thermotherapy is carried out by putting a region including portion intended to be heated of a living body between two opposed plate-like electrodes and applying a high-frequency current between the electrodes from a high-frequency power generator.

It has been difficult by the method to heat the portion intended to be heated, up to a temperature needed for therapy if it is situated at a deep inside, because those portions other than the portion intended to be heated may also possibly be heated since the high-frequency current flows substantially in parallel in the region between the opposed electrodes, because a subcutaneous fat layer tends to be heated more intensely than endotract organ tissues due to the difference of electrical constants (electrical conductivity, dielectric constant) between the subcutaneous fat layer and endotract organ tissues, and because there is a risk of patient's complaining of undesirable feeling of heat or of burning patient's epidermal tissues, etc. due to stronger generation of heat in the subcutaneous fat layer than in a portion adjacent to an electrode body.

In view of the above, there has been proposed, in the U.S. Pat. No. 4,676,258, a method of using a first electrode structure having a first electrode surrounded with a flexible and gastight bag-like member made of silicone rubber or the like and having a mechanism for supplying and discharging a coolant to the inside of the bag-like member and a second electrode structure, situating the first electrode structure (heating electrode structure) near the portion intended to be heated, while situating the second electrode structure having a second electrode (non-sensitive electrode structure) with an electrode surface larger by several times or more than the first electrode on the outer circumference of a living body, supplying a high-frequency electric current between the two electrodes, thereby forming an intense electric field distribution near the first electrode structure, selectively heating the portion intended to be heated, and monitoring the temperature at the surface of the living body or controlling the generated high-frequency power based on the information from a temperature sensor situated to the outer surface of the bag-like member.

However, in the above-mentioned method, the indication by the temperature sensor strongly undergoes the effect of the temperature of the coolant for cooling, which may lead to over heating or insufficient heating than required thus giving no insurance for the effective heating of the lesional portion.

Accordingly, it has been strongly demanded at present for the development of a method and an apparatus capable of performing a predetermined heating without the over heating or the insufficient heating and under a quantitative control in heating a living body by way of high frequency current.

SUMMARY OF THE INVENTION

The present invention has been achieved in view of the foregoing present situation and the object thereof is to provide a method of and an apparatus for heating capable of eliminating the patient's feeling of heat and pains due to the over heating by obtaining the reliable information on the temperature of the living body contacting with the bag-like member from a temperature sensor situated to the outer surface of an electrode body, and capable of performing safe and effective hyperthermia.

The foregoing object can be attained in accordance with the present invention by a method of heating a tract organ of the living body with high-frequency electric current, comprising the steps of: disposing a first electrode in a vicinity of an aimed portion to be heated of the tract organ, while disposing a second electrode on an outer surface of the living body; circulating a coolant into a space defined by an outer surface of the first electrode and an inner surface of the tract organ so as to fill the space with the coolant without contacting directly to the inner surface; supplying the high-frequency electric current to the first and second electrodes, while detecting a temperature of a living body tissue at a portion where the first electrode is disposed; and controlling a flow volume of the coolant so as to be substantially equal to that of a blood which flows in the living body tissue at the portion, while controlling a temperature of the coolant which is to be supplied into the space to a temperature range of the living body tissue at the portion, the coolant being an aqueous solution of salts at a concentration of 55 m eq/l to 100 m eq/l, and by an apparatus for heating a tract organ of the living body with high-frequency electric current, comprising: a first electrode structure so adapted as to be disposed to a vicinity of an aimed portion to be heated of the tract organ, and having a first electrode supported on an elongated flexible tube, a first flexible bag-like member surrounding the first electrode, first means for supplying and discharging a first coolant into and out of an inside of the first flexible bag-like member, and means attached to an outer surface of the flexible bag-like member for detecting a temperature of a living body tissue at a portion where the first electrode is disposed; a second electrode structure so adapted as to be disposed on an outer surface of the living body and as to selectively heat the aimed portion in association with the first electrode structure, and having a second electrode with an electrode area greater by 5 times or more than an area of the first electrode, a second flexible bag-like member disposed on a surface of the second electrode, and second means for supplying and discharging a second coolant into and out of an inside of the second flexible bag-like member; a high-frequency power source electrically connected to both of the first electrode and the second electrode for supplying the high-frequency electric current; and means connected to the first coolant supplying and discharging means for controlling a flow volume of the first coolant so as to be substantially equal to that of a blood which flows in the living body tissue at the portion where the first electrode structure is disposed, and for controlling a temperature of the first coolant which is to be supplied into the inside of the first flexible bag-like member to a temperature range of the living body tissue at the portion, the first coolant being an aqueous solution of salts at a concentration from 55 m eq/l to 100 m eq/l.

Since the apparatus of the present invention includes means for controlling a flow volume of a coolant supplied into a first electrode structure so as to be substantially equal to that of a blood which flows in a living body tissue at a portion where the first electrode structure is disposed while controlling a temperature of the coolant to a temperature range of the living body tissue at the portion, the coolant being an aqueous solution of salts of 55 m eq/l to 100 m eq/l, the apparatus of the present invention makes it possible to equalize a temperature of the coolant in the bag-like member of the first electrode structure to a temperature of the living body tissue at a portion where the first electrode structure is disposed, even upon application of a high frequency current, and enables to measure accurately a temperature of the outer surface of the tract organ without the effect of the temperature of the coolant and the effect of a spatial arrangement of the flexible tube supporting the first electrode in the case where the first electrode structure is disposed in an aimed portion of the tract organ, to thereby effect safely the hyperthermic treatment.

Further object and advantages of the present invention will be apparent from the following description of the preferred embodiment of the invention as illustrated in the accompanying drawings.

BRIEF DESCRIPTION OF THE DRAWINGS

FIGS. 1 and 2 are explanatory views for the concept of the high-frequency heating system;

FIG. 5 is a detailed explanatory view of the first electrode structure shown in FIG. 3;

FIG. 6 is an explanatory view for a cross section taken along line VI—VI in FIG. 5;

FIG. 7 is a cross sectional view taken along line VII—VII in FIG. 5 in a state where the bag-like member is deflated;

DESCRIPTION OF THE PREFERRED EMBODIMENT

Figure 3:
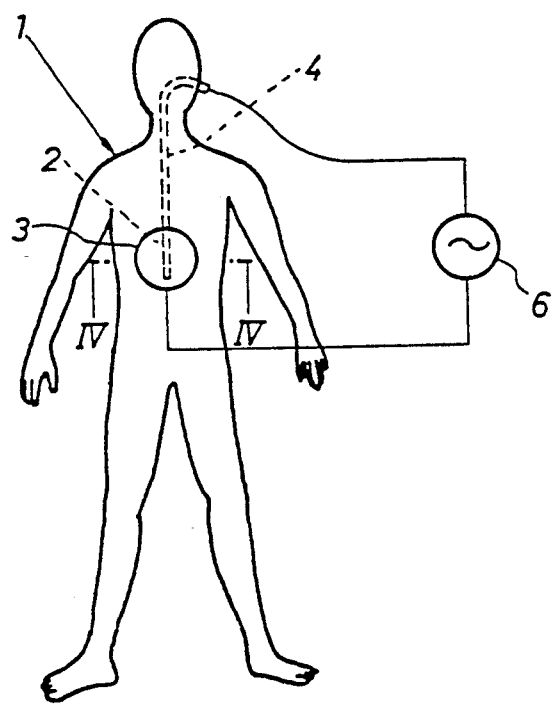
FIG. 3 is a schematic explanatory view for a preferred embodiment of the apparatus according to the present invention.
Figure 4:
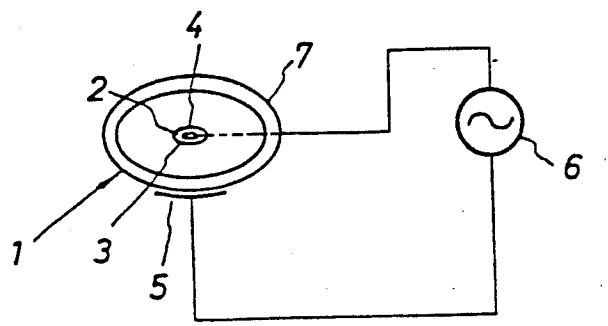
FIG. 4 is an explanatory view for the cross section taken along line IV—IV in FIG. 3.

In the conventional high-frequency heating method, hyperthermia is carried out, for example, as shown in FIGS. 1 and 2, by putting a region 3 including portion intended to be heated 2 of a living body 1 as a target between two opposed plate-like electrodes 4 and 5 and applying a high-frequency current between the electrodes 4 and 5 from a high-frequency power generator 6.

It has been difficult by the method to heat the portion intended to be heated 2, up to a temperature needed for therapy if it is situated at a deep inside, because those portions other than the portion intended to be heated 2 may also possibly be heated since the high-frequency current flows substantially in parallel in the region between the opposed electrodes, because a subcutaneous fat layer 7 tends to be heated more intensely than endotract organ tissues due to the difference of electrical constants (electrical conductivity, dielectric constant) between the subcutaneous fat layer and endotract organ tissues, and because there is a risk of patient's complaining of undesirable feeling of heat or of burning patient's epidermal tissues, etc. due to stronger generation of heat in the subcutaneous fat layer.

The second electrode structure (non-sensitive electrode structure) referred to in the present invention is, for example, such an electrode structure as disclosed in Japanese Patent Application Laying Open No. Sho 60-55966, which has a second electrode of a greater electrode surface area usually by 5 times and, preferably, by 10 times or more as compared with the first electrode of the first electrode structure (heating electrode structure) and has a remarkably small heating effect to a living body when it co-operates with the first electrode of the first electrode structure. The first electrode structure (heating electrode structure) has such a size as it can be disposed to the portion intended to be heated, for example, in endotract portion of a living body such as esophagus, stomach, vagina, etc. or at the surface of lesional mammary portion and is capable of selectively heating the desired living body tissue by supplying a high-frequency current between the first electrode incorporated into the first electrode structure and the second electrode of the second electrode structure to thereby form an intense electric field distribution in the vicinity of the first electrode structure.

A coolant having physical properties similar to those of the living body tissue to be heated will now be described.

The present inventors eagerly investigated how to precisely detect a temperature of surface of the endotract organ by a temperature sensor secured on a bag-like member of the first electrode structure and contacting with the surface of the endotract organ in the state where the coolant is introduced into the bag-like member, in accordance with the object of the present invention.

It was found to be a practical solution for precisely measuring the temperature of the surface of the endotract organ that physical properties of the coolant are so determined that the temperature of coolant becomes nearly equal to that of the surface to be measured of the endotract organ, even upon application of the high frequency current.

The following investigation is conducted from the standpoint that equalization of the temperature of the coolant with that of the surface to be measured of the endotract organ can be established by equalizing an amount of heat generation in the coolant within the bag-like member with that of the living body tissue outside the bag-like member.

Assuming the dielectric constant of the living body tissue outside of the film constituting the bag-like member to be $\epsilon_T$ and the loss factor thereof to be $\tan\delta_T$ and the electric field intensity at the vicinity thereof to be $E_T$ in the case of applying a high frequency voltage at a frequency f between a pair of electrodes, the power $P_T$ absorbed therein is represented as:

$$P_T = K \cdot f \cdot E_T^2 \cdot \epsilon_T \tan \delta_T \qquad (1)$$

Furthermore, assuming the electric field intensity, dielectric constant and the loss factor in the coolant to be $E_C$, $\epsilon_C$ and $\delta_C$ respectively, the electric power $P_C$ absorbed in the coolant is represented as:

$$P_C = K \cdot f \cdot E_C^2 \epsilon_C \tan \delta_C \qquad (2)$$

where K is a proportional constant.

While on the other hand, when a high-frequency voltage is applied between the first electrode of a smaller area (heating electrode such as endotract electrode) and a second electrode of a larger area (non-sensitive electrode such as external electrode), the electric field intensity is greater at the periphery of the first electrode of a smaller area (heating electrode) and attenuated as a distance from the first electrode increases. However, since the way of intensity attenuation is different depending on the shape and the configuration of electrodes and physical properties of the material put between the electrodes, it is not so easy to estimate the electric field intensity within the living body constituted by complicated substances.

However, since the thickness of the film constituting the bag-like member is sufficiently thin as compared to a distance between the electrodes in the apparatus according to the present invention, $E_T$ and $E_C$ can be considered to be almost equal with each other in the vicinity of the film.

Accordingly, by properly selecting the dielectric constant $\epsilon_C$ and the loss factor $\tan\delta_C$ of the coolant, it is possible to substantially equalize the electric power $P_T$ absorbed in the living body tissue near the first electrode structure with the electric power $P_C$ absorbed in the coolant. The proper selection of the dielectric constant $\epsilon_C$ and the loss factor $\tan\delta_C$ of the coolant can be attained by changing a concentration of a salt contained in the coolant.

In the present invention, the coolant means such a coolant as to absorb the electric power substantially equal with that in the living body tissue at the portion where the first electrode structure is disposed.

The kind of the coolant absorbing the electric power $P_C$ substantially equal to $P_T$ in a high frequency field, somewhat varies depending on the living body tissue as a target, and the usable coolant can include, for example, an aqueous solution at a concentration of a salt of 30 m eq/1–160 m eq/1, preferably, of less than 120 m eq/1 in the case of using a salt such as potassium chloride, sodium chloride and sodium carboxylate. Antibiotics or preservatives may be added as required to the coolant in the present invention as described above. Further, the salt may be used alone or as a mixture of two or more of them.

Explanation will then be made to the introduction and circulation of the coolant into and through the bag-like member of the first electrode structure. That is, the electric power $P_T$ absorbed in the tissue shown by the above-mentioned formula (1) is converted into a heat energy $(Q_P)$ of $1/J \times P_T$ per unit volume and unit time and a portion $(Q_B)$ of the thus converted heat energy is diffused to the peripheral portion of the tissue by way of a blood flow and heat conduction and, as a result, brings about a temperature increase $\Delta_T$ to the tissue.

The relationship between them is represented as:

$$Q_P - Q_B = \rho \cdot C \Delta T \qquad (3)$$

where $\rho$ and C are density and specific heat of the tissue, respectively.

The equation (3) should hold also with respect to the coolant. A heat energy diffused by heat conduction is a portion of the heat energy $Q_B$ represented by the equation (3) and is small as compared with heat energy carried away by the blood or the coolant, and hence can be neglected as a practical problem.

Accordingly, as density and specific heat of the coolant are approximately equal to those of the living body, the temperature increase of the coolant can also set approximately to $\Delta T$ by substantially equalizing the introducing and circulating amount of the coolant of the present invention into the bag-like member with the blood flow amount in the living body tissue.

The blood flow amount in the living body tissue, for example, in the case of muscle tissue is dependent on the temperature such as about 2 ml/min per 1 cm³ of the living body tissue at a temperature of 37° C., and about 7 ml/min at a temperature of 40° C. The blood flow amount in the living body tissue can be approximated by introducing and circulating the coolant of the present invention usually at a temperature from 37° C. to 43° C. by 1 to 15 times of an inner volume of the bag-like member per minute. The inner volume of the bag-like member means the inner volume of the bag-like member attained when it is extended or expanded by the coolant.

As mentioned above, in the apparatus of the present invention, the physical properties and flow volume of the coolant are so selected that a temperature increase of the coolant in the bag-like member can be substantially equalized with a temperature increase of the living body tissue to be heated upon application of a high-frequency current between the first electrode and the second electrode. Thus, in the case where the coolant is supplied into the bag-like member at a temperature substantially identical with a normal temperature of the living body tissue, a temperature of the coolant in the bag-like member can be substantially equalized with a temperature of the living body tissue contacting the bag-like member upon application of a high-frequency voltage, because the temperature increase of the coolant is set approximately to the temperature increase of the living body tissue as stated above. Accordingly, the temperature of a portion of the living body tissue to be heated can be accurately measured by the temperature sensor secured on the bag-like member without the effect of the coolant.

Since no substantial heating is recognized to the living tissue on the side of the second electrode structure, there are no particular restrictions to the circulation amount or the temperature of the coolant with respect to the second electrode structure.

The method according to the present invention can be provided by using, for example, a high-frequency heating apparatus which comprises an endotract electrode device as disclosed in Japanese Patent Application Laying Open No. Sho 60-119962 as the first electrode structure, and a medical electrode device as disclosed in Japanese Patent Application Laying Open No. Sho 60-55966 as the second electrode structure. A coolant having physical properties approximated to those of the living body tissue at a portion where the first electrode structure is disposed is used and means for supplying and discharging the coolant to and from the bag-like member is so provided that the coolant of 1 to 15 times of the inner volume of the bag-like member is circulated per minute in such high frequency heating apparatus.

In summary, the combination of the following three conditions makes it possible to equalize a temperature of the coolant in the bag-like member to a temperature of the living body tissue at a portion where the first electrode structure is disposed.

(i) A flow volume of the coolant introduced into the bag-like member of the first electrode structure is controlled so as to be substantially equal to that of a blood which flows in the living body tissue at the portion.

(ii) A temperature of the coolant supplied into the inside of the bag-like member is controlled to a temperature range of the living body tissue at the portion.

(iii) The coolant to be supplied into the inside of the bag-like member is an aqueous solution of salts at a concentration of 30 m eq/l to 160 m eq/l.

However, it is found out that the above three conditions for an accurate measurement of the temperature of the endotract tissue surface can be applied only in the case where the flexible tube supporting the first electrode is maintained in the substantially straight shape without being bent.

When the first electrode structure is inserted into an aimed portion of the endotract organ, the flexible tube is bent by the curved configuration of the endotract organ and a passage leading to the aimed portion. As a result, upon arranging the first electrode structure at the aimed portion of the endotract organ, the first electrode is situated in an eccentric state with respect to the bag-like member inflated by introduction of the coolant.

In the hyperthermic treatment, in particular, in treatment of the esophagus, such eccentric arrangement of the first electrode was frequently experienced, exerting a serious influence on measurement of temperature of the living body tissue being heated. It is possibly considered as a cause of said incorrect measurement of temperature that the eccentric arrangement of the first electrode can influence on a distribution of current intensity in the bag-like member as stated later.

On the other hand, in the case where environment surrounding the first electrode structure (for example, arrangement of the second electrode, and distribution of substances to be heated) is uniform, it is preferable that the first electrode structure is so provided as to enable to evenly heat the substances surrounding the bag-like member irrespective of the presence or absence of the eccentric arrangement of the first electrode.

As mentioned later, properties of the coolant required to realize such even heating are selected depending on a kind of the living body tissue as a target to be heated, a construction of the first electrode structure and so forth, and generally it is preferable to select an aqueous solution of salt at a concentration of 55 to 100 m eq/l for the purpose of evenly heating the living body tissue.

Fortunately, the above mentioned range of concentration of salt is within the range of concentration defined by the aforementioned condition (iii) for equalizing a temperature of the coolant in the bag-like member to a temperature of the living body tissue being heated.

Eventually, the use of the aforementioned conditions (i) and (ii) and an aqueous solution of the salt at the concentration mentioned above enables to measure accurately temperature of the target tissue even if the flexible tube is disposed in the eccentrically deformed state, and therefore to effect safely the hyperthermic treatment.

Then, explanation will be made to the preferred embodiment for the first electrode structure and the second electrode structure for the apparatus according to the present invention by way of the accompanying drawings.

FIGS. 5 through 7 show the details for the first electrode structure 4.

In FIGS. 5 through 7, a flexible two-channeled tube 8 made of silicone rubber in which a coolant supply channel 9 and a coolant discharge channel 10 are formed integrally.

At the top portion of the flexible tube 8, there are attached a flexible high-frequency electrode 11 and a flexible bag-like member 12 of a size capable of coming into contact with the inner wall of the tubular endotract organ without expansion of the flexible bag-like member. Connectors 13 and 14 for supplying and discharging a coolant are coupled integrally with the coolant supply channel 9 and the discharge channel 10 respectively. A portion where connectors 13 and 14 are respectively connected to the tube 8 is bonded by an adhesive and further covered with a heat-shrinkable tube 8a made of silicone.

The high-frequency electrode 11 as the first electrode is secured to the outer circumference of the tube 8 and it may be metal mesh, bellows, spiral member or the like so long as it has flexibility. The electrode 11 is formed to an axial length as equal to that of a tumour lesional portion.

A high-frequency lead wire 15 (for example, about 1 mm of outer diameter) is fixedly connected to the base end of the high-frequency electrode 11. The lead wire 15 is extended along the outer circumference of the two-channeled tube 8 near the base of the tube 8, and a connector 17 for connection with a power generator 7 is attached to its extended end.

The bag-like member 12 is formed into a cylindrical shape corresponding to the size and the shape of a tubular endotract near the lesional portion to which it is applied and, if desired, to the size and the shape of a portion narrowed by a tumour and the bag-like member 12 is secured to the outer circumference of the tube 8 on both of diametrically reduced ends 18 and 19 thereof so as to surround the electrode 11.

In a case where the first electrode structure 4 is applied to an esophagus, a bag-like member 12, for example, having 5-25 mm of outer diameter and 30-100 mm of length is used. In the case of inserting the first electrode structure 4 into the tract organ, the bag-like member 12 is deflated as shown in FIG. 7 and it is preferably folded, for example, as shown by the phantom line in FIG. 7.

The bag-like member 12 may be formed preferably with a molded tube or balloon made of silicone rubber.

Copper—constantan thermocouples 22, 23, 24, 25 and 26 as temperature detection means have thermocontacts 22a, 23a, 24a, 25a and 26a, and the thermocouples 22, 23, 24, 25 and 26 are secured by means of bonding to the outer surface of the bag-like member 12 such that they can be brought into a close contact with the film wall when the bag-like member 12 is expanded by the coolant.

The lead wires 22b, 23b, 24b, 25b and 26b are secured together with the high-frequency lead wire 15 and the base end 18 of the bag-like member 12 on the outer circumference of the tube 8 by means of a heat-shrinkable tube made of silicone without intersecting the lead wire 15.

A connector 28 for the lead wires 22b, 23b, 24b, 25b and 26b of the thermocouples comprises a 10—pin type receptacle 30 fixedly connected with the lead wires 22b, 23b, 24b, 25b and 26b and press-bonded at the cover portion, and a 10—pin type plug 32 which is detachable with the receptacle 30 secured to the outer circumference of the tube 8 and has lead wires 31 connected to a temperature measuring apparatus.

A coolant discharge hole 33 is communicated with the coolant discharge channel 10 formed in the tube 8, a coolant supply hole 20 is communicated with the coolant supply channel 9 formed in the tube 8, a top end portion 39 is disposed for guiding the insertion of the first electrode structure to the tract organ, a connector 34 for the coolant supply tube is connected with a pump 35 equipped with a flow control means through a cooler 36 equipped with a temperature control means. The connector 34 being so constituted as to be detachably attached to the connector 13. A connector 37 is so constituted as to be detachably attached to the connector 14 and as to discharge the coolant through the coolant discharge tube 38 or return the coolant to the pump 35.

Figure 8:
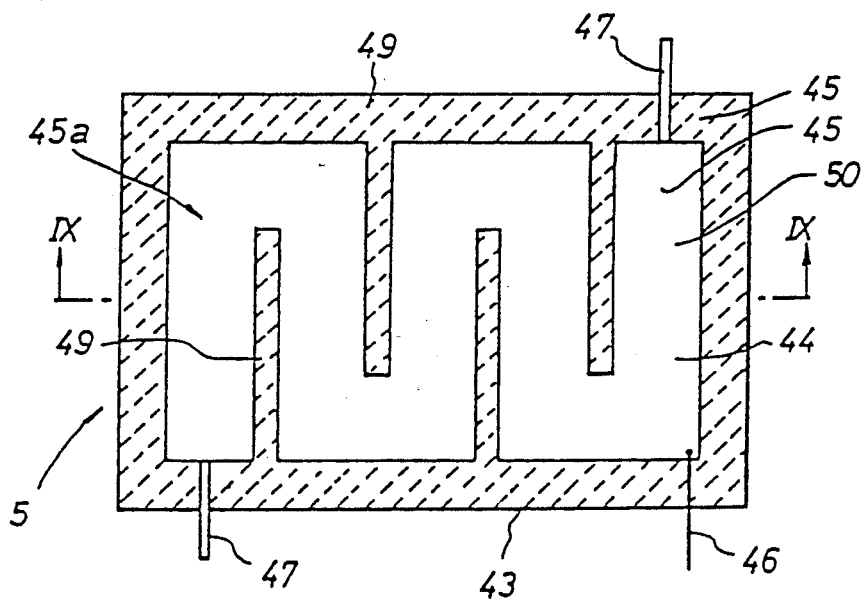
FIG. 8 is an explanatory view for the second electrode structure shown in FIG. 3.
Figure 9:
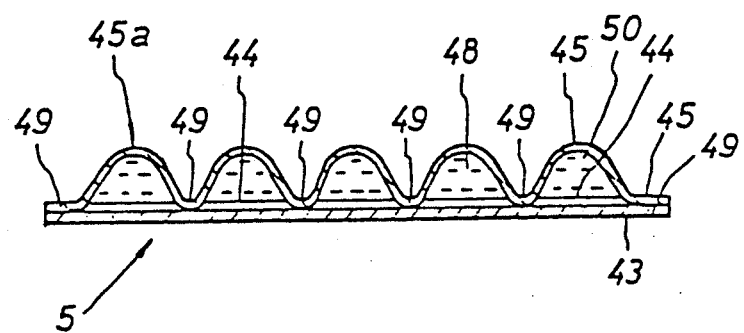
FIG. 9 is an explanatory view for the cross section taken along line IX—IX in FIG. 8.

FIGS. 8 and 9 show the second electrode structure 5 according to the present invention. In FIGS. 8 and 9, a substrate 43 comprises a nylon fabric coated with a silicone resin. In the drawing, are shown an electrode 44 made of a copper foil plate, an elastic silicone rubber sheet 45, a lead wire 46 connected to one end of a high-frequency power generator (not illustrated), and silicone tubes 47, 47 as supply and discharge tubes for the coolant 48. A portion or a region 49 shown by the broken hatched lines defines a portion where the substrate 43 and the rubber sheet 45 are bonded to each other for forming a coolant flow channel 50 in one direction between tubes 47, 47.

FIG. 9 is a cross sectional view taken along line IX—IX in FIG. 8 in a state where the coolant 48 is supplied, in which the upper side in FIG. 9 is brought into a close contact with the surface of a living body. In the foregoings, the bag-like member 45a is constituted with the sheet 45 and the substrate 43 and surrounds to electrode 44. The electrode 44 can be disposed on the outer surface of the substrate 43 covered with an insulating sheet (not shown).

The second electrode structure 5 can be brought into a good contact with the living body by the interaction between a fixing tool and the expansion of the silicone rubber sheet 45.

In the case of heating a lesional portion by the high-frequency heating apparatus according to the present invention, the temperature difference between the coolant in the bag-like member of the first electrode structure and the living body tissue which is in contact with the outer surface of the bag-like member is substantially eliminated irrespective of the presence or absence of deformation of the flexible tube. Therefore, according to the present invention, the temperature at the living body tissue can accurately be monitored based on the indication from the temperature sensor situated at the outer surface of the bag-like member of the first electrode structure irrespective of the level of the high-frequency power and the hyperthermia for the portion intended to be heated can be conducted safely.

The present invention will now be described more in details while referring to the examples.

EXAMPLE 1

A temperature sensor A is secured to the outer surface and a temperature sensor B is secured to the inner surface of a central portion of a bag-like member of a first electrode structure by means of adhesives respectively, in which the bag-like member made of silicone rubber and having a diameter of 15 mm and the length of 80 mm surrounds a helical electrode of a diameter of 8 mm and the first electrode structure is inserted into an esophagus.

While on the other hand, a second electrode structure having a coolant channel disposed on a copper plate of 120 mm width $\times$ 430 mm length is attached to a chest portion opposed to the esophagus.

Brine water at 70 m eq/l was used as the coolant, the temperature is controlled so as to be at 37° C. at the inlet of the first electrode structure and the circulation flow rate q is set to 50 ml/min. Since the volume v occupied by the coolant in the bag-like member is about 10 ml, the circulation amount per inner volume is (per minute) $q/v = 5$ times/min.

Figure 10:
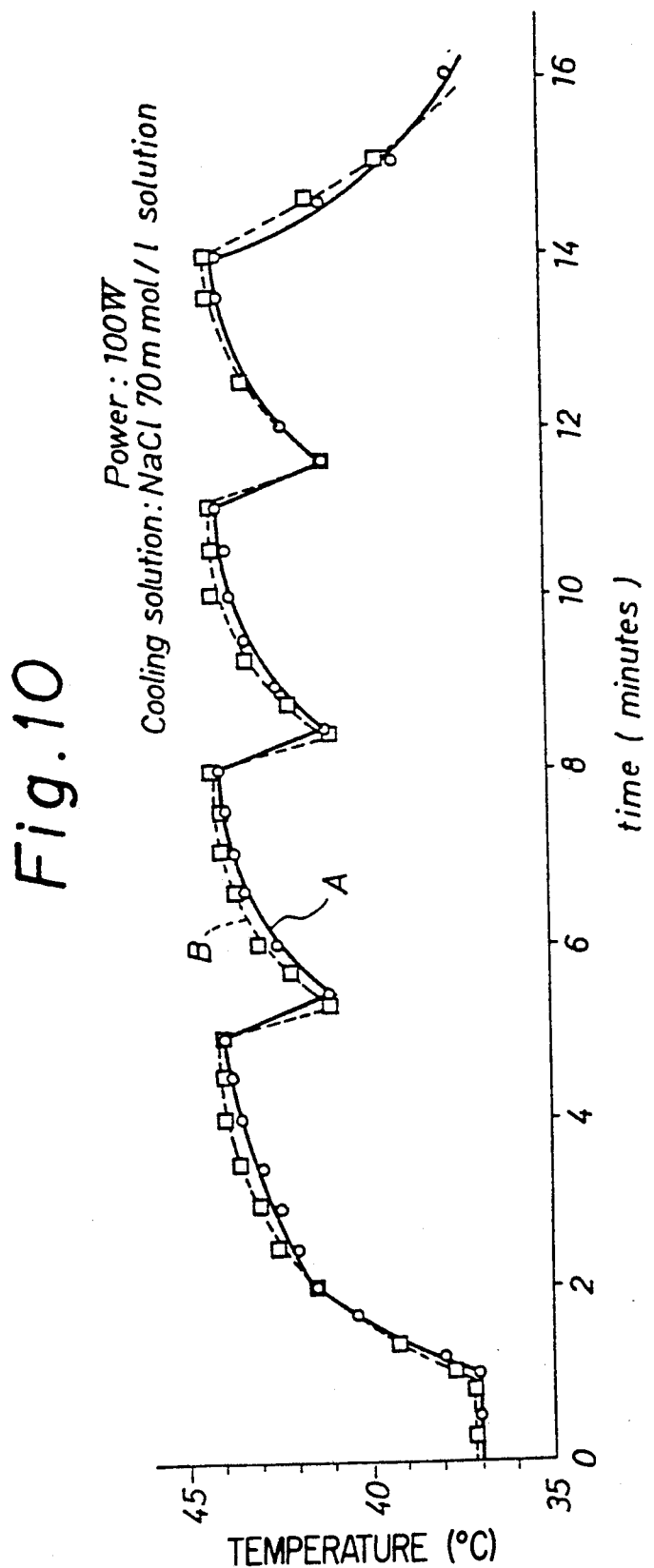
FIGS. 10 and 11 are charts showing a relationship between the time and temperature indication in the preferred embodiment according to the present invention.
Figure 11:
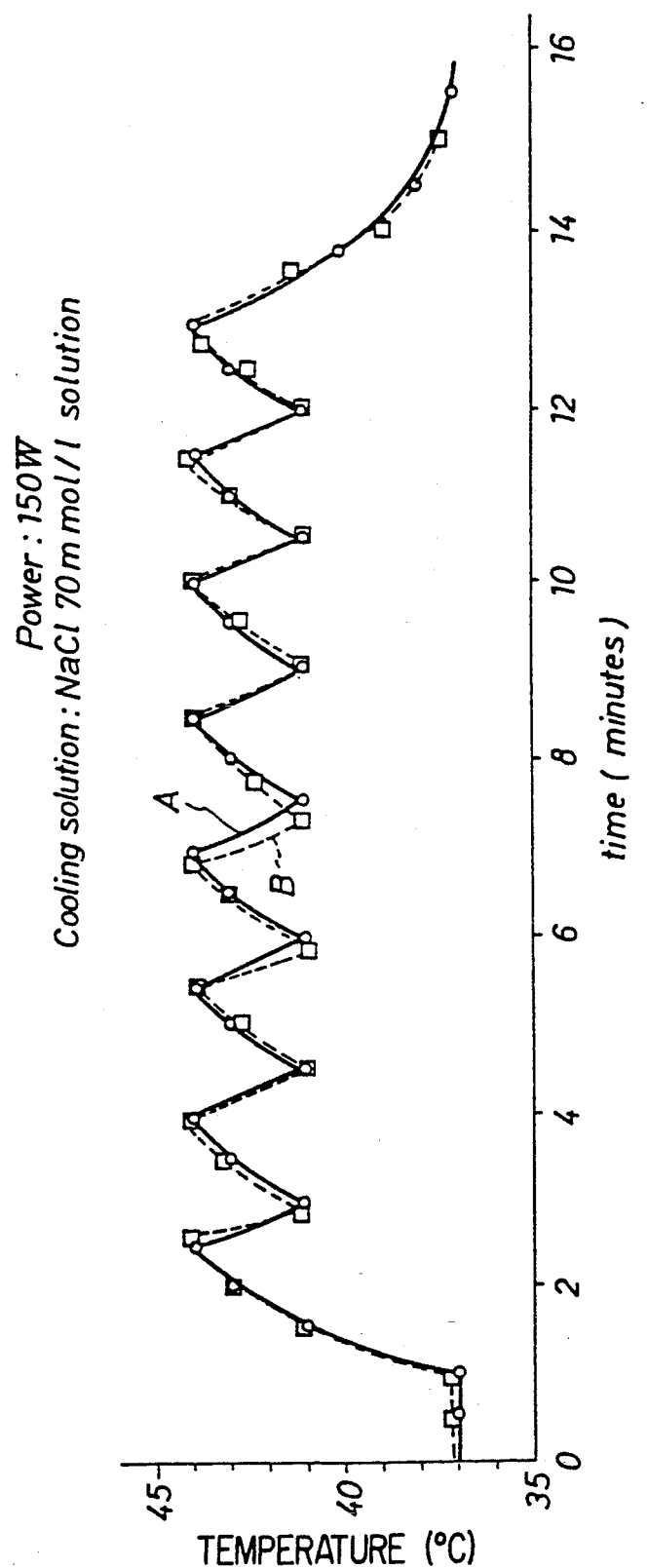

High-frequency current at 13.5 MHz is supplied at powers of 100 W and 150 W between the first electrode and the second electrode, in which the temperature difference shown by the sensors A and B is within 0.5° C. for both of the cases as shown in FIGS. 10 and 11.

Figure 12:
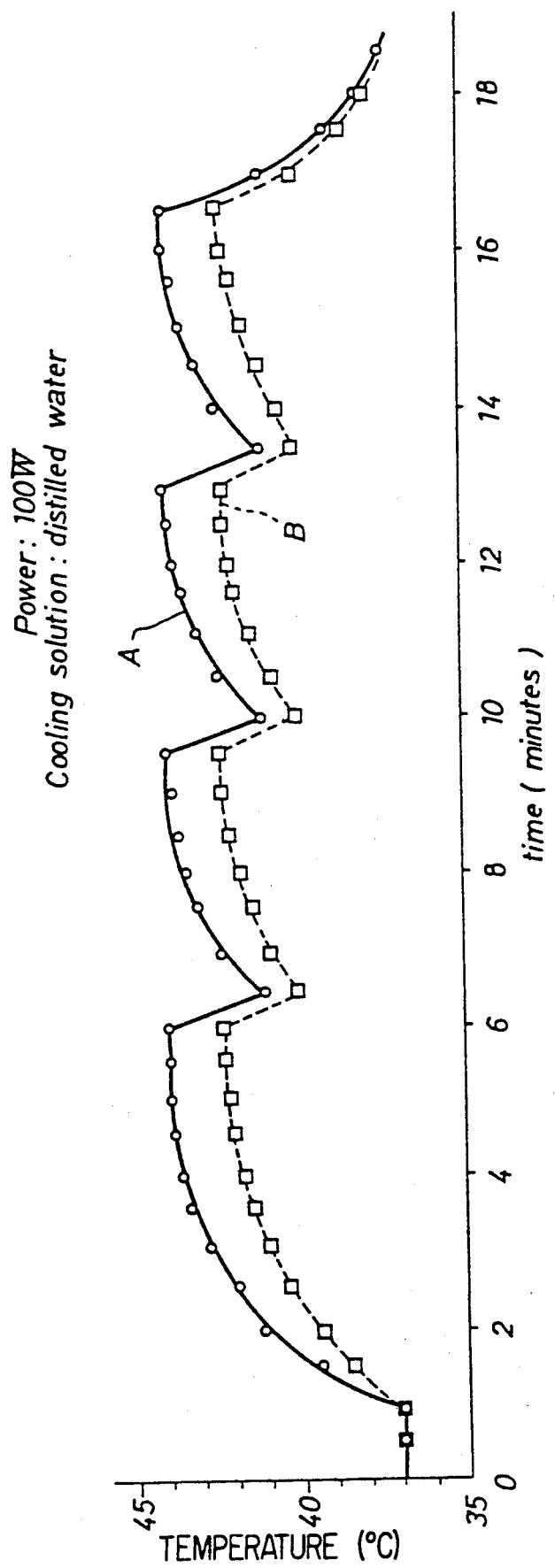
FIGS. 12 and 13 are charts showing a relationship between the time and temperature indication in a comparative embodiment.
Figure 13:
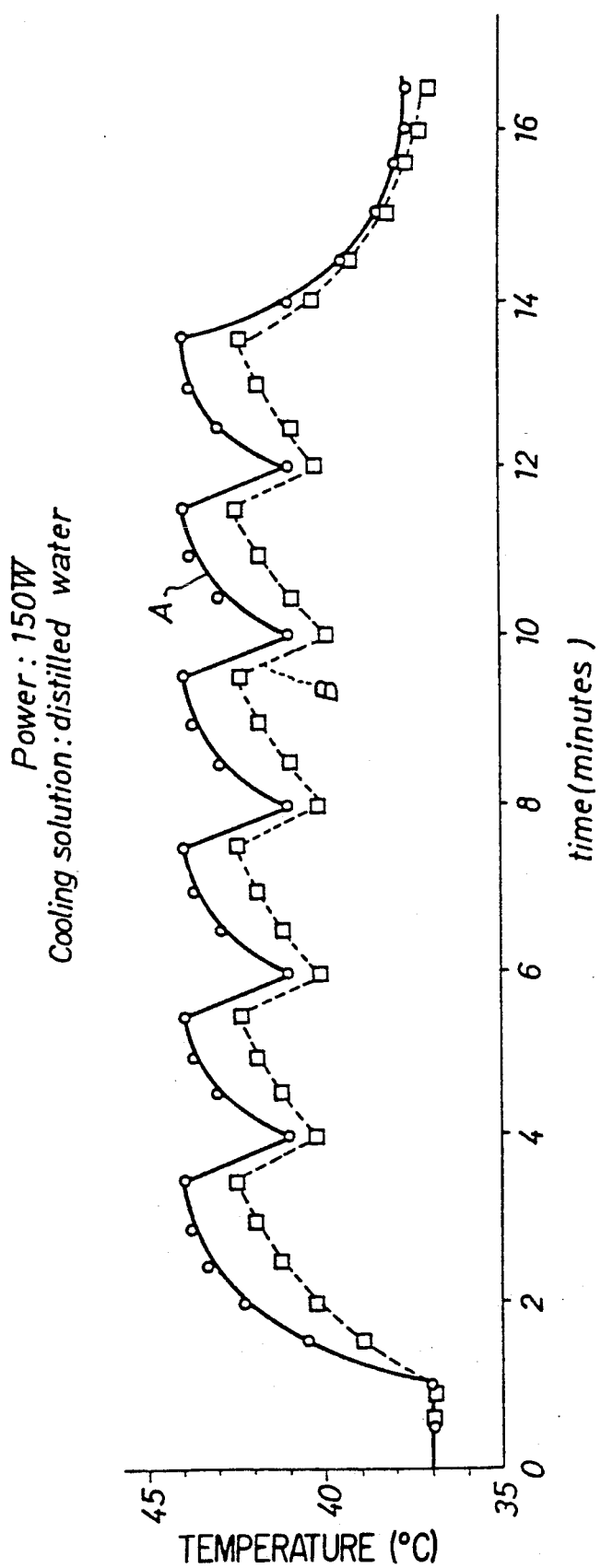

For the comparison, the result of the temperature measurement by the sensor A and the sensor B in the case of using distilled water as the coolant under the same conditions as described above are shown in FIGS. 12 and 13. The symbols ○ and □ show the indication temperatures of the sensors A and B respectively in the drawings.

In the case of a comparative example using distilled water as the coolant, it can be recognized that the temperature difference between the sensor A and the sensor B is remarkably greater as compared with the case of the example according to the present invention.

EXAMPLE 2

Figure 14:
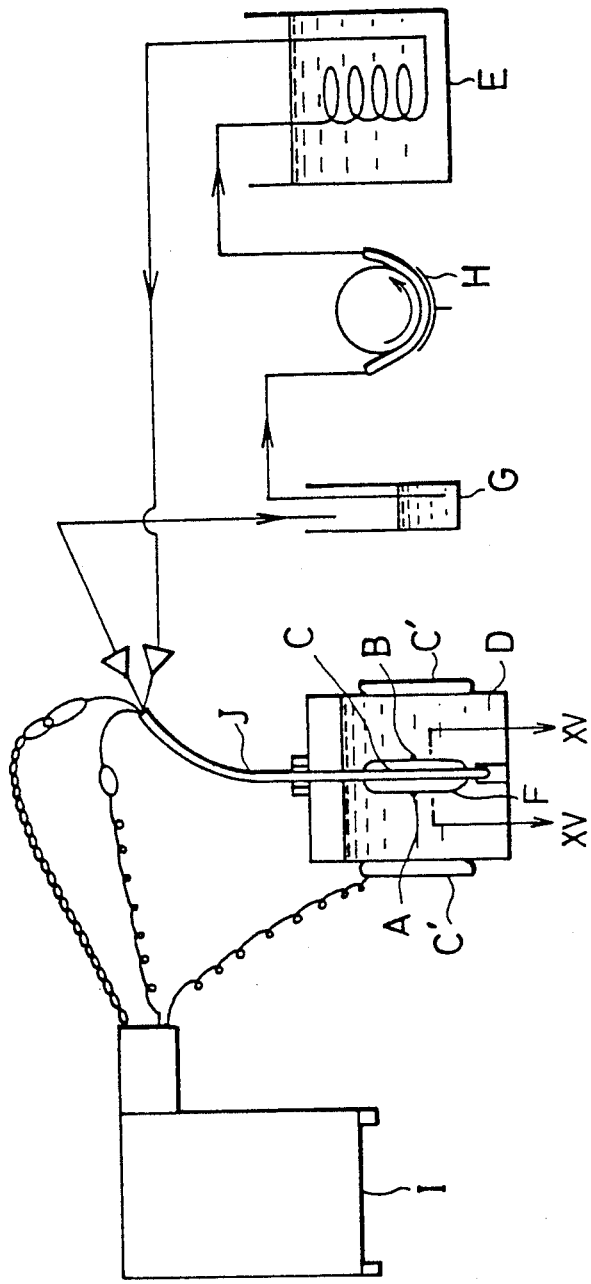
FIG. 14 is an explanatory view of an apparatus used in study on heating evenly the living body tissue.
Figure 15:
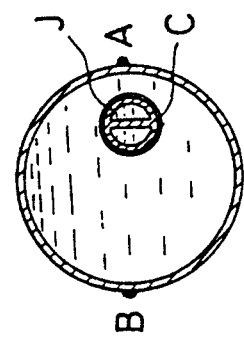
FIG. 15 is a cross section taken along line XV—XV in FIG. 14 and shows arrangement of sensors and a first electrode with respect to the bag-like member.

An experimental apparatus used in this example is illustrated in FIGS. 14 and 15.

The phantom D is made of Adherenori ®, which has a conductivity equivalent to that of muscles (the conductivity measured at 1 KHz: 4.2 mS/cm), and is formed into an outer size of 150 mm in diameter and 200 mm in height.

As the first electrode structure F, there is used a standard electrode structure for use in treatment of the esophageal cancer (made by Kureha Chemical Industry Co., Ltd.; catalog no. ES-15N; size of electrode: 7 mm in outer diameter, 80 mm in length; size of bag-like member: 15 mm in inner diameter, 100 mm in length, about 13.8 cm$^3$ in inner volume). The first electrode structure F is vertically disposed in a central position of the phantom D formed into the shape of a cylinder.

A copper foil plate is disposed around all outer circumferential surface of a container having an inner diameter of 150 mm and receiving the phantom D, to form a cylindrical second electrode C'. Coolant is circulated into a bag-like member between the copper foil plate and container.

A sensor A is secured with an adhesive on an outer surface of longitudinally central portion of the bag-like member constituting the first electrode structure, and a sensor B is secured with the adhesive on an outer surface of the bag-like member so as to oppose to the secured sensor A. The flexible tube J and the first electrode C supported on the flexible tube J are arranged in such a manner as to be eccentrically shifted on the side of the sensor A by about 2.5 mm from the normal position thereof as shown in FIG. 15.

Endoradiotherm-100 ® I (made by Kureha Chemical Industry Co., Ltd.), which includes a temperature measurement unit, is used as a high-frequency electric power source unit.

A thermostat bath E is maintained at a temperature of 38.6° C. The coolant is circulated into the bag-like member at a flow rate of 2.88 l/hr through the thermostat both E and a coolant reservoir G by a pump H. The flow rate of 2.88 l/hr corresponds to 3.5 times of an inner volume of the bag-like member per minute. Hundred mls of each of aqueous solutions at various kinds of concentrations of sodium chloride are used as the coolant.

In each run, the first electrode C and the second electrode C' are operated for two minutes by a power of 200W outputted from Endoradiotherm-100 ® I, and temperature indications of the sensors A and B are observed respectively.

The difference between two temperature indications of the sensors A and B is observed relative to each of coolants at various kinds of concentrations of sodium chloride.

The thus obtained differences ($\Delta T_{A-B}$) between the temperatures indicated by the sensors A and B are respectively shown corresponding to the kinds of coolants in Table 1.

In run No. 9, a saline solution is used as the coolant.

TABLE 1

| No. | Coolant | Concentration of Salt in Coolant (m eq/l) | $\Delta T_{A-B}$ (°C.) |
|---|---|---|---|
| 1 | Aqueous Solution of NaCl | 1.6 | 6.1 |
| 2 | " | 3.1 | 5.6 |
| 3 | " | 4.7 | 4.6 |
| 4 | " | 9.2 | 3.6 |
| 5 | " | 18.5 | 2.3 |
| 6 | " | 37 | 0.8 |
| 7 | " | 74 | 0 |
| 8 | " | 125 | −0.5 |
| 9 | " | 154 | −0.7 |

From the above Table-1, it is apparent that the whole contents of the bag-like member comes to function as an electrode with increase of concentration of sodium chloride in the coolant and, as a result, the above-mentioned even heating can be attached at a specified concentration of sodium chloride. And also, it is seen from the Table-1 that the difference ($\Delta T_{A-B}$) is reversed at the sign thereof when the concentration of the salt exceeds the specified value.

It is reasonable to consider the reversal of the temperature difference as follows.

In the case of coolant containing sodium chloride at a relatively low concentration, an electrical resistivity of the coolant mainly influences on high-frequency current intensity on the bag-like member. Accordingly, a region having a shorter distance between the first electrode and the bag-like member shows a less electrical resistivity, and hence a temperature of point A becomes higher as compared with that of point B (refer to FIG. 15).

As the coolant in the bag-like member approaches such a state as to function as an electrode with increase of the concentration of sodium chloride in the coolant, the effect of electrical resistivity of the coolant on the current intensity on the bag-like member gradually decreases, so that the value of $\Delta T_{A-B}$ becomes smaller with increase of the concentration of sodium chloride.

When the concentration of sodium chloride in the coolant reaches the specified value, the value of $\Delta T_{A-B}$ becomes zero.

In the case of the concentration of sodium chloride exceeding the specified value, the sign of $\Delta T_{A-B}$ is reversed by uneven distribution of electrical resistivity caused by a flow state of the coolant.

Apart from the cause for the reversal of temperature difference, the result shown in the Table-1 indicates an optimum condition for evenly heating the living body tissue. The optimum condition obtained from the experiment using the phantom which has conductivity of 4.2 mS/cm equivalent to that of muscles is that an aqueous solution of the salt at a concentration of 74 m eq/l (electrical conductivity of 8.0 mS/cm) is used as the coolant.

The electrical conductivity of the aqueous solution shows a value about two times as much as that of the phantom. Such difference in electrical conductivity between the aqueous solution of specified concentration and the phantom can be comprehended in the case of considering that a convection of the aqueous solution in the bag-like member makes temperature distribution of the coolant therein uniform, and that an intensity of electric field in the vicinity of the first electrode is greater than that in the vicinity of the bag-like member.

The optimum concentration of the salt in the aqueous solution for realizing such even heating slightly varies depending on the living body tissue as a target to be heated and the construction of the first electrode structure, and hence a preferable range of concentration of the salt is 55 to 100 m eq/l.

Favorably, the preferable range is within the range of concentration defined by the aforementioned condition (iii) as stated above. Eventually, the use of the aforementioned conditions (i) and (ii) and an aqueous solution of salt at concentration mentioned above enables to measure accurately temperature of the target tissue even if the flexible tube is disposed in the eccentrically deformed state, and therefore to effect safely the hyperthermic treatment.

Many widely different embodiments of the present invention may be constructed without departing from the spirit and scope of the present invention. It should be understood that the present invention is not limited to the specific embodiment described in this specification, except as defined in the appended claims.

What is claimed is:

1. A high-frequency heating device comprising:
    a first electrode structure adapted as to be disposed to the vicinity of a portion intended to be heated, and having a first electrode;
    a flexible bag-like member surrounding said first electrode;
    a circulating fluid supplying and discharging means connected to said flexible bag-like member for supplying a circulating fluid to an inside of said flexible bag-like member and for discharging said supplied circulating fluid from said inside of said flexible bag-like member;
    a temperature detecting means attached to an outer surface of said flexible bag-like member for detecting a temperature of the living body tissues at said portion intended to be heated;
    a second electrode structure so adapted as to be disposed on an outer circumference of a living body and as to selectively heat said portion at the periphery of said first electrode structure in association with said first electrode structure, and having a second electrode with an electrode area greater by 5 times or more than the area of said first electrode;
    a high-frequency power source connected to said first electrode and said second electrode for supplying a high-frequency current to said first and second electrodes; and
    a temperature controlling means for controlling a temperature of a circulating fluid within said flexible bag-like member such that said temperature of said circulating fluid within said flexible bag-like member becomes approximately equal to an aimed temperature to which said living body tissues are intended to be heated and wherein said circulating fluid supplying and discharging means is adapted to control a flow rate of said supplied circulating fluid such that said flow rate of said supplied circulating fluid is substantially equal to a blood flow rate in said living body tissues, and said circulating fluid being an aqueous solution of a salt at a concentration from 30 m eq/l to 160 m eq/l.

2. A high-frequency heating device according to claim 1, in which a flow rate of said supplied circulating fluid per minute is from 1 to 15 times the volume of an inner volume of said flexible bag-like member.

* * * * *